(12) United States Patent
Wiedenmann et al.

(10) Patent No.: US 7,361,620 B2
(45) Date of Patent: Apr. 22, 2008

(54) CATALYTICALLY ACTIVE LAYER

(75) Inventors: Hans-Martin Wiedenmann, Stuttgart (DE); Frank Stanglmeier, Ceske Budejovice (CZ); Karl-Hermann Friese, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 261 days.

(21) Appl. No.: 10/284,887

(22) Filed: Oct. 31, 2002

(65) Prior Publication Data

US 2003/0111341 A1 Jun. 19, 2003

(30) Foreign Application Priority Data

Nov. 7, 2001 (DE) .................... 101 54 638

(51) Int. Cl.
*G01N 27/407* (2006.01)
(52) U.S. Cl. .................... 502/101; 204/424; 205/783.5
(58) Field of Classification Search ........ 204/291–293, 204/424; 205/794.5, 783.5–786; 429/40–45, 429/229, 231; 502/101
See application file for complete search history.

(56) References Cited

U.S. PATENT DOCUMENTS

| | | | | |
|---|---|---|---|---|
| 3,429,751 A | * | 2/1969 | Heuse | .................. 205/666 |
| 5,045,520 A | * | 9/1991 | Curry-Hyde et al. | ........ 502/301 |
| 5,368,713 A | * | 11/1994 | Friese et al. | ................. 204/429 |
| 5,876,867 A | * | 3/1999 | Itoh et al. | ..................... 429/44 |
| 6,087,296 A | | 7/2000 | Harper | |
| 6,215,030 B1 | * | 4/2001 | Morikawa et al. | .......... 568/814 |

FOREIGN PATENT DOCUMENTS

| | | |
|---|---|---|
| DE | 1 129 291 | 5/1962 |
| DE | 689 24 960 | 4/1989 |
| DE | 691 14 895 | 3/1991 |
| DE | 40 33 388 | 4/1992 |
| GB | 1000826 | * 8/1965 |

* cited by examiner

*Primary Examiner*—Kaj K. Olsen
(74) *Attorney, Agent, or Firm*—Kenyon & Kenyon LLP

(57) ABSTRACT

A catalytically active layer that is used, for example, as an electrode for a solid electrolyte-based sensor element of a gas sensor for determining a gas component in a gas mixture. The catalytically active layer includes a metallic component, that includes a noble metal in the form of platinum, rhodium, and/or palladium, and additionally a base metal. At least a portion of the originally present base metal is replaced by cavities in the metallic component.

4 Claims, 1 Drawing Sheet

CATALYTICALLY ACTIVE LAYER

FIELD OF THE INVENTION

The present invention relates to a catalytically active layer and to a method of manufacturing a catalytically active layer.

BACKGROUND INFORMATION

Electrodes of electrochemical gas sensors often fulfill a dual function by being used both for the electron transfer in contact with a surrounding medium and for the catalytic conversion of gas components at their surface. In the case of ceramic sensors, it is especially difficult to achieve long-lasting and sufficient catalytic activity of the catalytically active layers functioning as electrodes. The original catalytic activity of the layers is often lost as early as in the sintering processes during the manufacture of the gas sensor; in addition, when working with highly corrosive gas mixtures, the same thing occurs during the operation of the gas sensor.

German Patent No. 42 40 267 describes that the electrodes of an exhaust gas sensor be impregnated with a solution of a catalytically active metal such as platinum or rhodium after sintering the gas sensor. In this manner, a highly active electrode is obtained despite the prior sintering process. However, this procedure does not change the insufficient stability of the electrodes during long-term operation in corrosive gas mixtures.

German Patent No. 40 33 388 describes a layer system for gas sensors where a catalytically active electrode of the gas sensor is coated with a protective layer including substances that absorb harmful contaminants. In this manner, the stability of the gas sensor electrodes is enhanced. This arrangement requires a multilayer structure.

German Patent Application No. 1 129 291 describes a Raney catalyst made of a silver alloy including silver and up to 60 wt. % aluminum. This Raney catalyst is used as an electrode for fuel elements. Raney catalysts are also used for hydrogenation and dehydrogenation reactions where mainly Raney nickel is of importance. In addition, Raney silver, Raney cobalt, Raney iron, Raney copper, and Raney molybdenum are referred to as catalysts.

It is an object of the present invention is to provide a catalytically active layer that has high and long-lasting catalytic activity.

SUMMARY OF THE INVENTION

The catalytically active layer according to an example embodiment of the present invention includes a metallic component that includes both a noble metal in the form of platinum, rhodium, or palladium, and a base metal. The addition of a base metal to the catalytically active metals platinum, rhodium, and/or palladium results in the enhancement of the noble metal's catalytic activity, which is high anyway. Furthermore, the catalytically active layer includes cavities that increase the available catalytically active surface of the layer and thus its overall catalytic activity.

When using the catalytically active layer as an electrode in solid electrolyte-based gas sensors, catalytically highly active electrodes are obtained, which catalyze the reaction of the individual exhaust gas components with one another even at low temperatures. This may be advantageous, for example, in the warm-up phase of an internal combustion engine.

Thus, in an exemplary embodiment of the present invention, the catalytically active layer additionally includes a ceramic component, which provides intimate bonding of the catalytically active layer with the ceramic base material of the gas sensor when the catalytically active layer is used in ceramic gas sensors.

The method of manufacturing a catalytically active layer may provide that intensive blending and bonding of the components embedded in the catalytically active layer are achieved, while numerous small cavities having a large surface area are produced within the layer in a simple manner. This is achieved by manufacturing the catalytically active layer by the Raney principle, where the noble metals platinum, rhodium, and/or palladium are intimately bonded with a base metal to form a metal-containing component and subsequently the base metal is dissolved away, at least partially, from the metal-containing component with the formation of cavities.

A method of manufacturing the catalytically active layer is facilitated when an alloy of the noble metal with the base metal is formed as the metallic component.

In an exemplary embodiment, the base metal is dissolved away using a solution which additionally includes substances that absorb harmful contaminants. All those gaseous or liquid compounds which negatively affect the catalytic activity of the layer in any manner are considered harmful contaminants. The addition of substances that absorb harmful contaminants enhances the stability of the catalytically active layer thus obtained.

DETAILED DESCRIPTION

Figure 1:
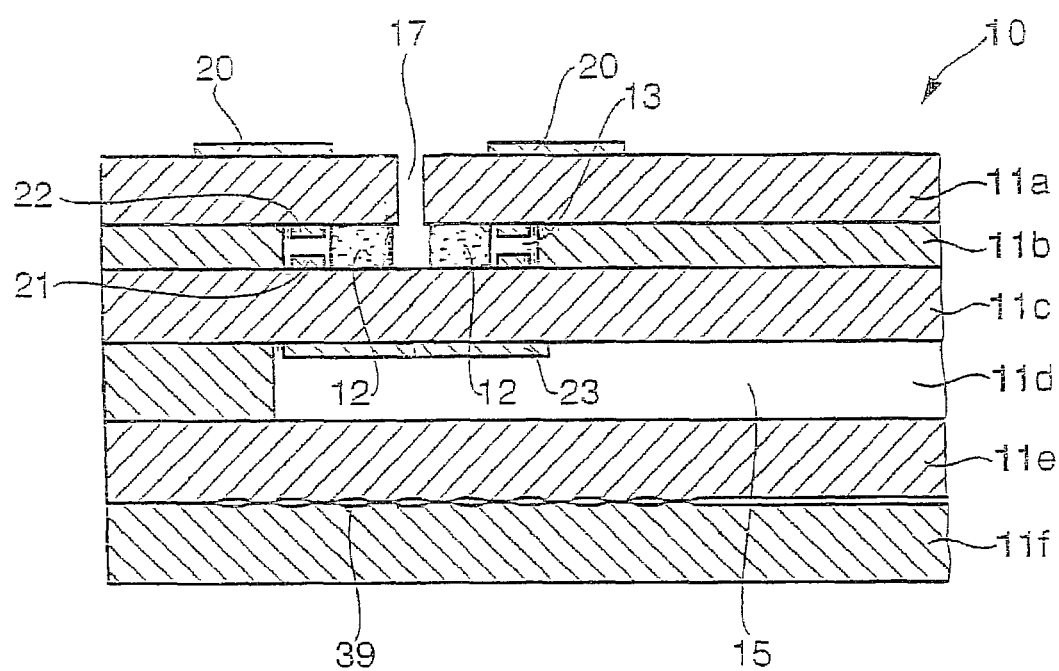
FIG. 1 shows a longitudinal section through a sensor element for determining gas components in gas mixtures, at least one of the electrodes of the sensor element including a catalytically active layer according to an example embodiment of the present invention.

A catalytically active layer according to an example embodiment of the present invention includes a metallic component. The metallic component includes at least one of the noble metals platinum, rhodium, palladium, and optionally other noble metals. In addition, the metallic component includes a base metal. Base metals include all metals which, according to the electrochemical potential ranking, have a lower oxidation potential than the above-mentioned noble metals. The metals zinc and aluminum may be considered here. The metallic component is formed by intimate bonding of the noble metal(s) with the base metal(s). This may be achieved either by using an alloy of the noble metal(s) with at least one base metal or by depositing the at least one base metal or noble metal on metallic particles.

Another option for forming the metallic component is by mixing at least one noble metal and at least one base metal, both in powdered form, with one another and subsequently obtaining the metallic component by thermal treatment. Another option includes applying the noble metal(s) on a substrate, exposing the substrate to thermal treatment in order to fix the noble metal and subsequently impregnating the composite thus obtained with a salt solution of one or more base metals, and optionally subjecting it to an additional thermal treatment in order to form the metallic component.

In order to achieve the desired catalytic activity of the catalytically active layer, a portion of the base metal is subsequently dissolved away from the metallic component. This may be accomplished chemically, for example, by treating with aqua regia or electrochemically by electrically contacting the catalytically active layer and connecting it as the anode.

The catalytically active layer may be made entirely of the metallic component, but it may also include an added ceramic component. This may provide the advantage that the catalytically active layer, when used in ceramic gas sensors, for example, is permanently bonded with the ceramic base material of the gas sensor by a sintering process. The same ceramic base material on which the gas sensor itself is based is also used as the ceramic component. In order to further enhance the stability of the catalytically active layer, it may be treated during or after the manufacturing process with a solution of one or more substances that absorb harmful contaminants. These substances, also referred to as getters, bond sulfur, zinc, or lead compounds occurring in exhaust gases of internal combustion engines and prevent the catalytic activity of the catalytically active layer from being negatively affected. Magnesium chloride, titanium chloride, lithium nitrate, and aluminum nitrate, converted into the corresponding oxides or mixed oxide systems via appropriate thermal post-treatment of the catalytically active layer, are suitable in this context as substances that absorb harmful contaminants.

In the following, five exemplary embodiments of catalytically active layers are given and their manufacturing is described.

In the first exemplary embodiment, the catalytically active layer is produced in the form of a cermet electrode by mixing together 60 vol. % of a metallic component and 40 vol. % of a ceramic component in powdered form and regrinding the mixture, optionally with the addition of a thinning oil. The suspension is applied to a substrate, for example, a pre-sintered solid electrolyte sensor body in a conventional manner by spraying, brushing, rolling, dipping, laminating, casting, or printing in a layer thickness of 10 to 30 μm, dried, and sintered for five hours at 1500° C. A powdered mixture including 90 wt. % platinum and 10 wt. % commercially available zinc powder is used as the metallic component. Partially or fully stabilized zirconium dioxide, for example, is used as the ceramic component, optionally with the addition of up to 4 wt. % aluminum oxide. The catalytically active layer is impregnated with aqua regia in order to activate it, first at a partial vacuum of 100 mbar and then raising the pressure to 1 bar at a temperature of approximately 50-80° C. Subsequently it is rinsed with distilled or deionized water.

In a second exemplary embodiment, the catalytically active layer is manufactured as in the first exemplary embodiment; however, initially pure platinum powder is used as the metallic component, and the catalytically active layer is treated after the sintering process with a 10% magnesium chloride solution and thermally treated again.

In a third exemplary embodiment, the catalytically active layer is manufactured as in the second exemplary embodiment; however, an equimolar solution of lithium nitrate and aluminum nitrate is used as the salt solution for impregnating. The catalytically active layer is dipped into this solution for approximately three minutes at room temperature, and subsequently allowed to drip-dry for ten minutes. The impregnated layer is then heated for two hours, for example, at 1000° C. under air to form the metal oxides.

In a fourth exemplary embodiment, manufacturing occurs as in the first exemplary embodiment; however, instead of adding 10 wt. % commercially available zinc powder, 5 wt. % commercially available aluminum powder is used.

In a fifth exemplary embodiment, the catalytically active layer is manufactured as in the first exemplary embodiment; however, a platinum-zinc powder mechanically pre-alloyed in a grinding process and including a zinc content of 10 wt. % is used as the metallic component.

FIG. 1 shows a planar sensor element of an electrochemical gas sensor, which is used, for example, for determining the oxygen content of a combustion exhaust gas. Sensor element 10 includes, for example, a plurality of oxygen ion-conducting solid electrolyte layers 11$a$, 11$b$, 11$c$, 11$d$, 11$e$, and 11$f$, which are configured as ceramic sheets made of $ZrO_2$ partially or fully stabilized with $Y_2O_3$.

Layer level 11$b$ of sensor element 10 includes a measuring gas space 13 and an additional layer level 11$d$ includes, for example, an air reference channel 15, for example, whose one end extends outside the planar body of sensor element 10 and is connected to a reference gas atmosphere.

An external pump electrode 20, which may be covered with a porous protective layer (not shown) and is arranged in an annular form around a gas inlet orifice 17, is arranged on the large surface of sensor element 10 directly facing the measuring gas on solid electrolyte layer 11$a$. The corresponding internal pump electrode 22, which also has an annular configuration, matching the annular geometry of measuring gas space 13, is arranged on the side of solid electrolyte layer 11$a$ facing measuring gas space 13. Both pump electrodes 20, 22 together form a pump cell.

Opposite internal pump electrode 22, a measuring electrode 21 is located in measuring gas space 13, this measuring electrode also having an annular shape, for example. A corresponding reference electrode 23 is arranged in reference gas channel 15. Measuring electrode 21 and reference electrode 23 together form a Nernst cell, i.e., concentration cell.

During the operation of the sensor element, the pump voltage across pump cell 20, 22 is varied so that a constant potential difference is established across the electrodes of Nernst cell 21, 23. The pump current flowing between electrodes 20, 22 is used as the measuring signal of the sensor element.

A porous diffusion barrier 12 is arranged upstream in the diffusion direction of the measuring gas from internal pump electrode 22 and measuring electrode 21 in measuring gas space 13. Porous diffusion barrier 12 forms a diffusion resistance for the gas diffusing to electrodes 21, 22.

Furthermore, a resistance heater 39 is embedded between two electrical insulation layers in the ceramic base body of sensor element 10. The resistance heater is used for heating sensor element 10 to the required operating temperature.

In order to ensure that the thermodynamic equilibrium of the measuring gas components is established at the electrodes, all electrodes 20, 21, 22, 23 used may be configured as catalytically active layers according to one of the preceding exemplary embodiments. It is, however, also possible, to configure only electrodes 20, 21, 22, exposed to the gas mixture, as catalytically active layers according to the present invention and electrode 23 as a platinum layer. The electrode materials are used as cermet for all electrodes in the conventional manner for sintering with the ceramic sheets.

However, the use of such a catalytically active layer is not restricted to electrochemical gas sensors for determining oxygen. In principle, the catalytically active layers are suited for any type of catalytically active electrode. Additional applications include, for example, heterogeneous catalysis and catalytic purification of combustion exhaust gases.

What is claimed is:

1. A method of manufacturing a catalytically active layer including a metallic component, comprising:

bonding at least one of platinum, rhodium, and palladium as a noble metal with a base metal to form the metallic component; and forming a plurality of cavities in the metallic component by dissolving the base metal, at least partially, from the metallic component wherein the metallic component is formed by depositing the noble metal on a plurality of metallic particles, the plurality metallic particles comprising the base metal.

2. The method of claim 1, wherein the catalytically active layer includes a ceramic component.

3. The method of claim 1, wherein the base metal is dissolved by impregnating the catalytically active layer with a solution that includes a plurality of substances that absorb a plurality of harmful contaminants.

4. A method of manufacturing an electrode of a solid electrolyte-based sensor element of a gas sensor for determining a gas component in a gas mixture, comprising:

bonding at least one of platinum, rhodium, and palladium, as a noble metal with a base metal to form a metallic component; and forming a plurality of cavities in the metallic component by dissolving the base metal, at least partially, from the metallic component wherein the metallic component is formed by depositing the noble metal on a plurality of metallic particles, the plurality of metallic particles comprising the base metal.

* * * * *